United States Patent
Galas et al.

(10) Patent No.: US 8,103,522 B1
(45) Date of Patent: Jan. 24, 2012

(54) SYSTEM AND METHOD FOR CALCULATING CLAIM REIMBURSEMENT RECOMMENDATIONS

(75) Inventors: Thomas E. Galas, Coppell, TX (US); David L. Potash, Nashville, TN (US); Thomas P. Ralston, Bonita Springs, FL (US); Lisa K. Jamsen, Parachute, CO (US)

(73) Assignee: National Care Network LLC, Irving, TX (US)

( * ) Notice: Subject to any disclaimer, the term of this patent is extended or adjusted under 35 U.S.C. 154(b) by 477 days.

(21) Appl. No.: 12/163,813

(22) Filed: Jun. 27, 2008

Related U.S. Application Data

(60) Provisional application No. 60/947,069, filed on Jun. 29, 2007.

(51) Int. Cl.
*G06G 50/00* (2006.01)
(52) U.S. Cl. .......................................... 705/2
(58) Field of Classification Search ................. 705/2, 3; 364/406
See application file for complete search history.

(56) References Cited

U.S. PATENT DOCUMENTS

| | | | |
|---|---|---|---|
| 4,667,292 A * | 5/1987 | Mohlenbrock et al. | 705/2 |
| 6,208,973 B1 | 3/2001 | Boyer et al. | |
| 6,792,410 B1 | 9/2004 | Donovan et al. | |
| 2004/0243438 A1 | 12/2004 | Mintz | |
| 2005/0033612 A1 | 2/2005 | Donovan et al. | |
| 2006/0265251 A1 * | 11/2006 | Patterson | 705/3 |

* cited by examiner

*Primary Examiner* — Gerald J. O'Connor
*Assistant Examiner* — John Pauls
(74) *Attorney, Agent, or Firm* — Baker & Daniels LLP

(57) ABSTRACT

The present invention provides a system and method for calculating claim reimbursement recommendations. A medical claim is received and grouped to an rDRG or a median cost value. All similar hospital cases based on the same rDRG are identified. Costs of all comparison cases are then adjusted based on hospital's wage index. Using a pre-selected methodology, the initial target reimbursement amount is calculated. Any applicable override rules and/or inflation factors are then applied to arrive at the reimbursement amount. All relevant information on reimbursement amount and how the amount was calculated is presented to the user.

30 Claims, 12 Drawing Sheets

HOME :: CLAIM SEARCH :: HIPPA :: LINKS :: CONTACT US :: LOGOUT

Summary

- Total Submitted Charges: $39,913.42
- Hospitals Cost of Care: $10,915.00 (Estimates using your hospitals most recently available cost report submitted to CMS and applying revenue-center level cost-to-charge ratios)
- Medicare Standard Reimbursement Amount for this refined DRG at your hospital: $11,159.30
- Data/Sight Reimbursement Amount: $27,898.25
- The Data/Sight Reimbursement Amount was based on: Reimbursement amount equal to 250% of standard Medicare reimbursement for this reined DRG at this hospital.

*Notes: For all comparison cases outside your community, costs were adjusted using wage indices based on the hospitals prevailing labor costs.

[<<Back]     [Main Menu]     [Search for New Claim]     [Logout]     [Print>>]

FIG. 3

SYSTEM AND METHOD FOR CALCULATING CLAIM REIMBURSEMENT RECOMMENDATIONS

CROSS-REFERENCE TO RELATED APPLICATIONS

The present application claims priority under 35 U.S.C. §119(e) of U.S. Patent Provisional Application Ser. No. 60/947,069, entitled "SYSTEM AND METHOD FOR CALCULATING CLAIM REIMBURSEMENT RECOMMENDATIONS", filed Jun. 29, 2007.

BACKGROUND OF THE INVENTION

1. Field of the Invention

The present invention generally relates to health care claim reimbursement systems and methods.

2. Description of the Related Art

The approaches described in this section could be pursued, but are not necessarily approaches that have been previously conceived or pursued. Therefore, unless otherwise indicated herein, the approaches described in this section are not teachings or suggestions of the prior art to the claims in this application and are not admitted to be prior art by inclusion in this section.

There was a time when people needed medical attention they paid the doctor directly for his or her professional services. Times have changed. Modern medicine can work miracles our grandparents never dreamed of, but sometimes at a staggering price. The provision of critical healthcare treatment is often regarded as a basic human right, regardless of whether the individual has the means to pay—at the same moment some forms of healthcare treatment cost more than a typical family's life savings. These days most Americans rely on a third party—either a private insurer, or a public governmental entity—to help them finance the cost of their medical needs.

Today, the healthcare industry is a huge business, with many large managed care companies traded on the stock exchange. The healthcare industry accounts for approximately $1.5 trillion in market revenue. The added complexities of the current health care system and the sheer volume of medicines being manufactured and administered has resulted in a long payment cycle. Today's health care organizations and individual providers face challenges processing and getting reimbursed for medical insurance claims, as well as determining fair reimbursement amounts.

SUMMARY OF THE INVENTION

The present invention involves cost containment methods to ensure appropriate healthcare reimbursements that are innovative, flexible, recognized and accepted while being in a transparent format to all parties. The present invention provides a process to determine the true value of a medical occurrence at the specific claim level ensuring appropriateness of reimbursement, while also ensuring a valid method of reporting findings through an informational source accessible by all parties: payor, patient, and hospital.

One embodiment of the present invention begins with the receipt of a medical claim and entry into the Data iSight system. An in-patient hospital claim is grouped to a Refined Diagnosis Related Group (rDRG). An rDRG system is a case-mix system that classifies cases into levels of severity and complexity based on the presence of comorbidities and complications and their impact on resource use. The next step is to identify all 'like' hospitals, thus creating a benchmark as described below. Then, all like cases based on the same rDRG are identified. Costs of all comparison cases are then adjusted based on hospital's wage index. Using a pre-selected method, the initial target reimbursement amount is calculated. Any applicable override rules and/or inflation factors are then applied to arrive at the reimbursement amount. All relevant information on reimbursement amount and how the amount was calculated is presented to the user.

The process for out-patient claims differs since hospitals are required to use HCPCS (HCFA Common Procedure Code System) rather than DRG's when billing for outpatient services. The out-patient process examines each claim line and then benchmarks each HCPCS to a national or peer group median cost value. The claim is received and is processed through the CMS Out-Patient Code Editor (OCE) to review coding accuracy. Cost of care is then determined by accessing cost reports from the Healthcare Cost Report Information System (HCRIS) cost reporting system. Costs of all comparison cases are then adjusted based on hospital's wage index. Using a pre-selected method, the initial target reimbursement amount is calculated by summing the line item medial benchmark costs from the claim and applying an additional margin factor. Any applicable override rules and/or inflation factors are then applied to arrive at the reimbursement amount. All relevant information on reimbursement amount and how the amount was calculated is presented to the user.

The reimbursement accounting provided by this system has both transparency and consistency. The users of the system are shown both the basis for comparison and the methodology of reimbursement of a claim. The reimbursement amounts are consistent because the claims are first categorized with particularity apparent to the user, and are then compared to analogous payments and normalized by both removing outlier amounts and adjusting for local factors.

Advantageously, the system may be deployed over a network or the internet, and the various components of data needed to perform the desired calculations may be supplied remotely. Another feature involves an override to the reimbursement amount. For example, one override may be that the reimbursement amount must be at least to a level where a certain percentage of benchmark hospitals are profitable. Another override may dictate that the reimbursement amount cannot exceed the billed charges.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 3 is a sample screen shot of the output displayed to the user.

Figure 1:
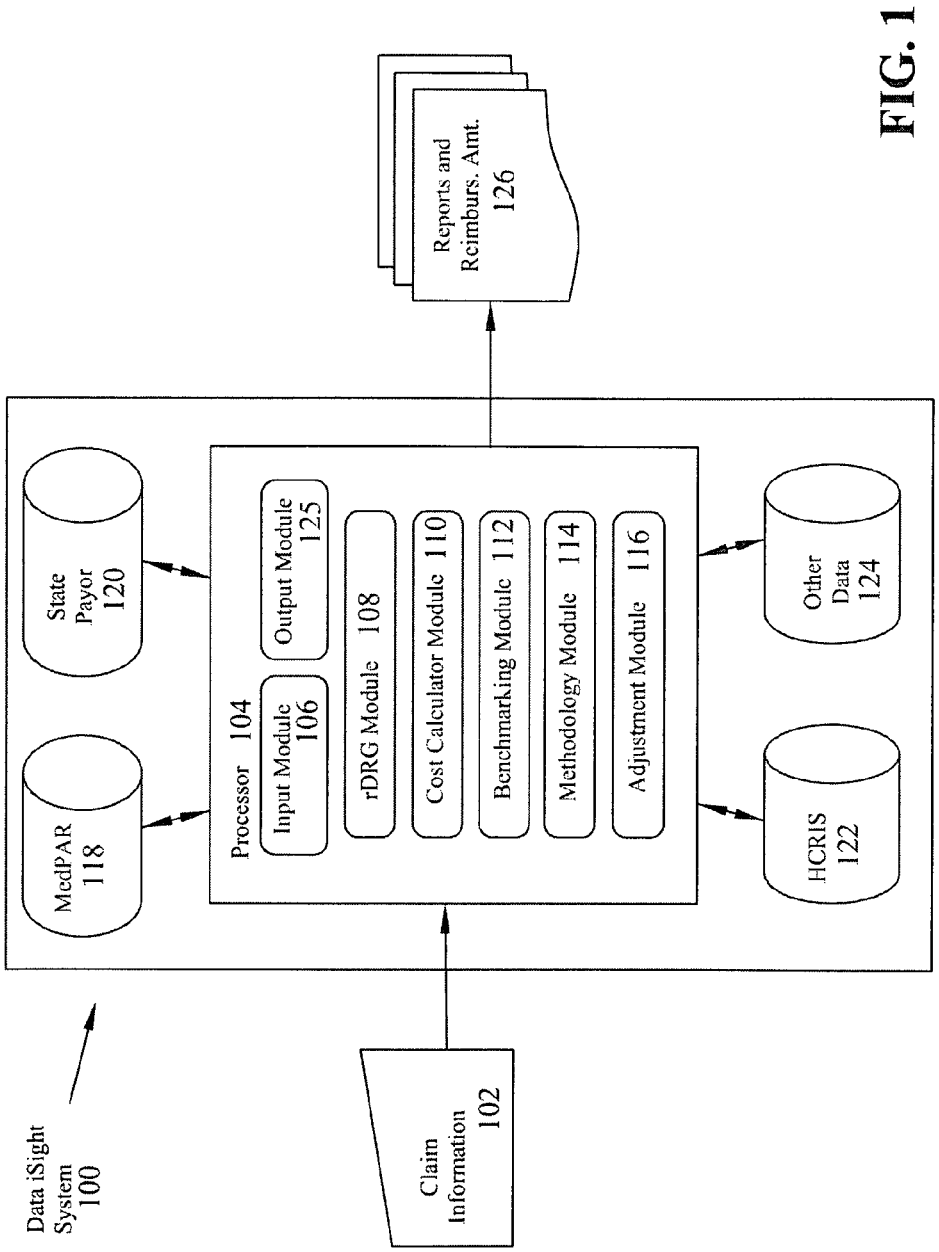
FIG. 1 is a schematic diagram of the system for determining the reimbursement amount.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DESCRIPTION OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

The detailed descriptions that follow are presented in part in terms of algorithms and symbolic representations of operations on data bits within a computer memory representing alphanumeric characters or other information. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory; rather they represent specific electronic structural elements that impart a physical organization on the information stored in memory. More than mere abstraction, the data structures are specific electrical or magnetic structural elements in memory that simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical signals.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus. In particular, various general-purpose machines may be used with programs written in accordance with the teachings herein, or it may prove more convenient to construct more specialized apparatus to perform the required method steps. The required structure for a variety of these machines will appear from the description below.

The present invention deals with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects. Objects may also be invoked recursively, allowing for multiple applications of an objects method until a condition is satisfied. Such recursive techniques may be the most efficient way to programmatically achieve a desired result.

An operator may stimulate a collection of interrelated objects comprising an object-oriented program by sending a message to one of the objects. The receipt of the message may cause the object to respond by carrying out predetermined functions that may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment.

The term "Browser" refers to a program which is not necessarily apparent to the user, but which is responsible for transmitting messages between the workstation and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information that is formatted in a Standard Generalized Markup Language ("SGML") or a HyperText Markup Language ("HTML"), both being scripting languages that embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method). "XML-RPC" is a remote procedure call protocol encoded in XML. It is considered the ancestor of SOAP. It is a very simple protocol, defining only a handful of data types and commands, and the entire description can be printed on two pages of paper.

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a handheld device and a desktop computer either via wires or wirelessly. Synchronization ensures that the data on both the handheld device and the desktop computer are identical.

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces.

The term "hospital" is used to refer to the health care provider organization, or provider, which is generally a hospital but may also be another type of facility, like an emergency medical facility, an outpatient care clinic, a doctor's office, or other type of health care facility. "MedPAR" or "Medicare Provider Analysis Review" (file) is a hospital discharge database containing records for Medicare beneficiaries who were discharged in a given year. Centers for Medicare and Medicaid Services (CMS) maintains the MedPAR database. "DRG" is a Diagnosis Related Group while "rDRG" is a Refined Diagnosis Related Group (output from Yale Refined DRG methodology grouper, where RDRG is a registered trademark of Health Systems Consultants, Inc.), that is a diagnosis group also rated for severity. "APC" refers to Ambulatory Payment Classifications. "ASC" refers to Ambulatory Surgical Case. "Bill Type" refers to the Uniform Billing codes used to classify types of claims. "CCR" refers to the cost to charge ratio. "DiS" refers to Data iSight. "FReD" refers to both the fair reimbursement determination and the software tool that computes this amount. "HCPCS" refers to the Healthcare Common Procedure Coding System (HCPCS) which is a set of health care procedure codes based on the American Medical Association's Current Procedural Terminology (CPT) required for outpatient billing under the Health Insurance Portability and Accountability Act of 1996 (HIPAA). "HCRIS" refers to the Healthcare Cost Report Information System managed by CMS (the agency that administers Medicare/Medicaid). "HDA" refers to Hospital Detail Analysis. "OCE refers to the CMS Out-Patient Code Editor publically available through CMS. "Pricer" refers to the software tool that computes the amount paid by Medicare to providers. "Revenue Code" refers to the uniform billing code to categorize services into like groupings of services. "Severity" refers to the severity classification output from rDRG grouper software.

Generally, the method starts with the receipt of a health care reimbursement claim, which is checked for the Bill Type. Such a claim has a cost estimation performed for hospital specific costing, as described below. An inpatient claim is grouped for rDRG and Severity assignment, while outpatient claims are grouped to APC assignments and ASC to corresponding ASC assignments. The claim is sent to the appropriate Medicare Pricer according to the Bill Type, and to the appropriate Data iSight tool for pricing.

For costing, both a provider number and a Revenue Code are used. Using the Medicare provider number, departmental CCRs may be identified from the stored HCRIS files and used as a basis for determining the hospital's cost to provide the care described on the claim. The methodology screens for outliers or incorrect CCRs as part of the costing procedure. If an appropriate CCR associated with the provider number is not located, an average cost for all providers in the state may be used as a basis for costing. The average cost for the state may also be used if there is no provider number where the user enters a state.

One embodiment of an exemplary system of the present invention is depicted in FIG. 1. Data iSight System 100 includes Processor 104 with several modules and databases. Claim information 102 is received by Input Module 106, either through manual entry or an automated process. rDRG Module 108 performs the rDRG assignment. Cost Calculator Module 110 performs the cost of care calculations. Benchmarking Module 112 performs the benchmarking of the hospital facilities. Methodology Module 114 performs the reimbursement calculations using the pre-selected methodology. Adjustment Module 116 applies any overrides or other factors (such as an inflation factor) to the reimbursement amount.

Several different databases may be used in the method. For example, a database including MedPAR files 118 represent all Inpatient Medicare discharges in the country. Outpatient Medicare claims are accessed utilizing the Medicare OPPS File and the Outpatient Standard Analytical file. Additionally, State All-Payor files 120 constitute another database where records are collected from participating states and represent all discharges in those states. Further, Healthcare Cost Report Information System (HCRIS) files 122 populate yet another database which include cost reports submitted to CMS annually by individual hospitals, signed and attested to by the hospital Chief Financial Officer. Another source is All-Payor database 124 representing externally purchased accumulated claims data. These sources provide detailed data on nearly all the acute care hospitals in the nation. Reports and reimbursement results 126 are provided to the user via Output Module 125. While the embodiments of the invention are described using these various databases, the methodology of the present invention may be implemented using less than all of these databases, and may also use other databases not mentioned in this specification or existing at this time. Optionally, these databases may be augmented by a new database comprised of reimbursements made by Data iSight System 100

Figure 2A:
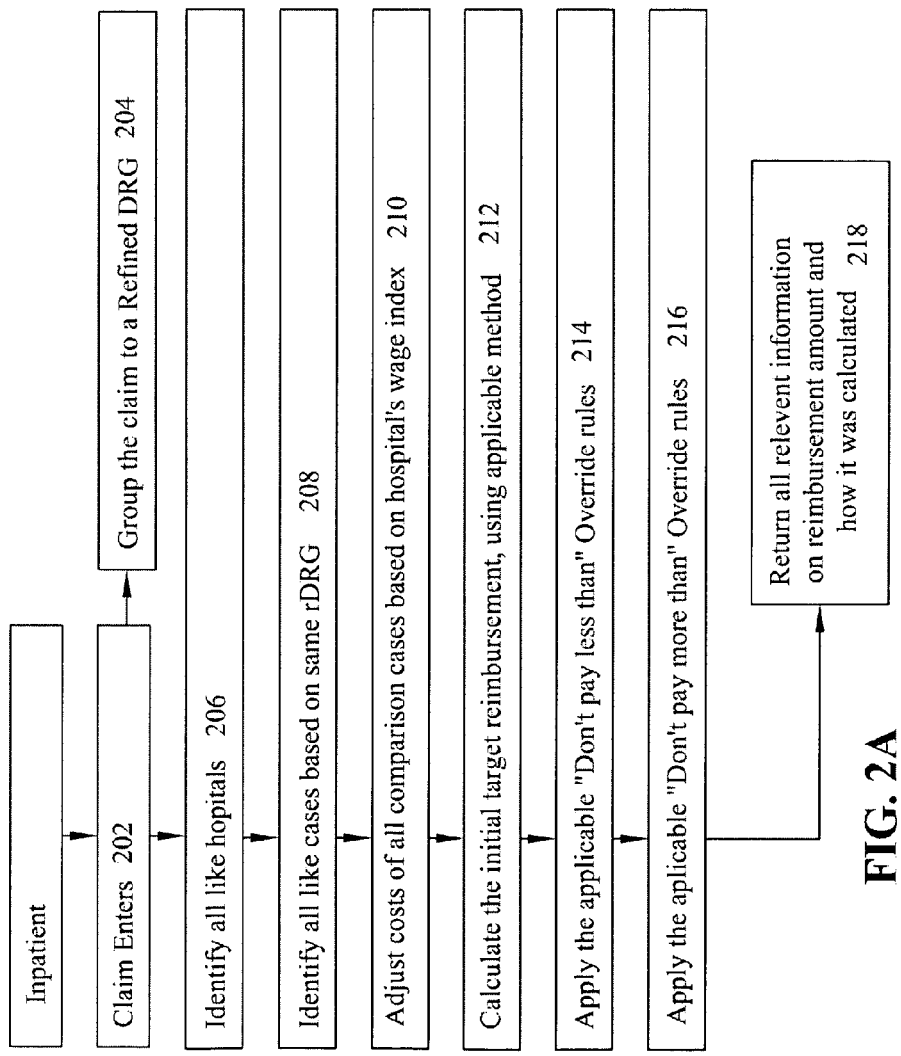
FIG. 2A is a flow chart diagram illustrating an exemplary method for determining the reimbursement amount for in-patient medical services.
Figure 2B:
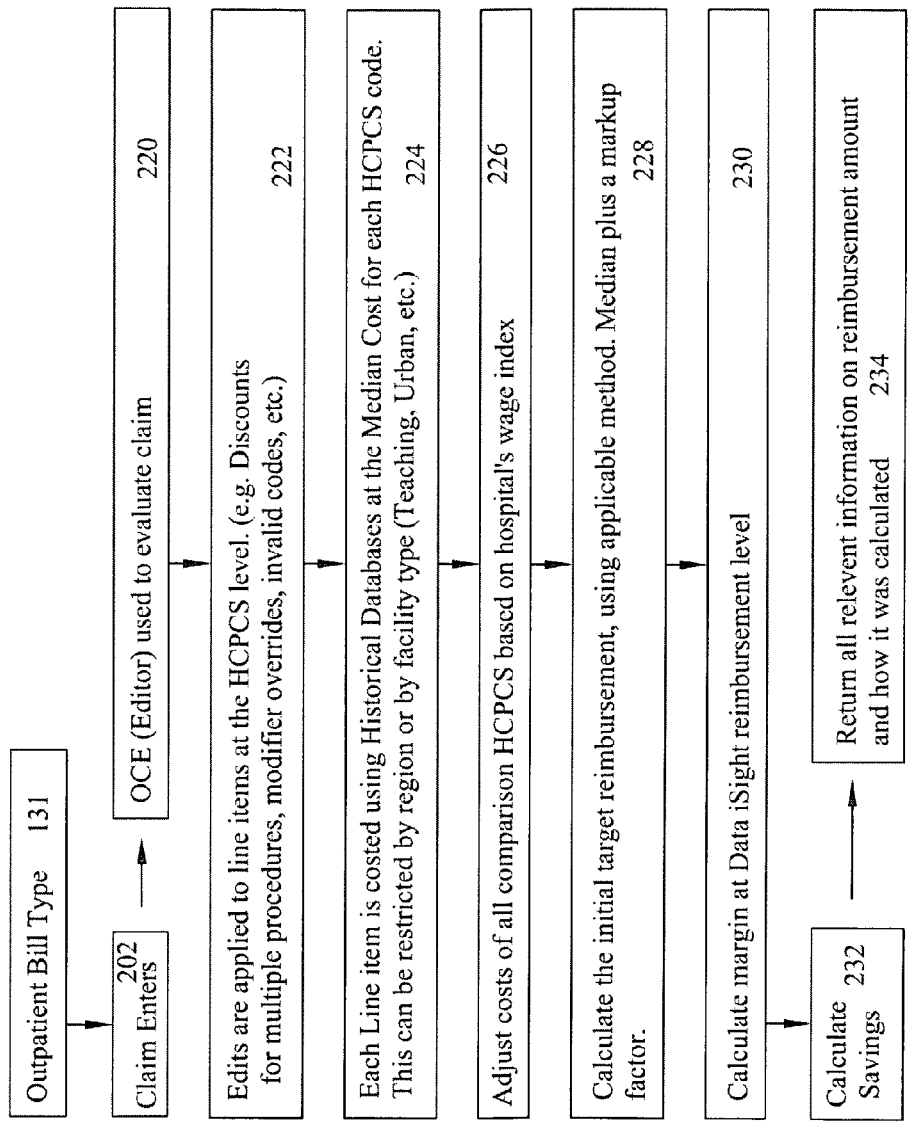
FIG. 2B is a flow chart diagram illustrating an exemplary method for determining the reimbursement amount for out-patient medical services.

A high-level description of the reimbursement method is depicted in FIGS. 2A and 2B. In both Figures, the method begins with the receipt of a medical claim and entry into Data iSight (step 202). FIG. 2A represents an in-patient claim. Inpatient claims are grouped to a Refined DRG (rDRG) (step 204). The next step is to identify all 'like' hospitals (step 206). Then, identify all like cases based on same rDRG (step 208). Costs of all comparison cases are then adjusted based on hospital's wage index (step 210). Using a pre-selected method, the initial target reimbursement amount is calculated (step 212). Any applicable override rules and/or inflation factors are then applied (steps 214, 216) to arrive at the reimbursement amount. All relevant information on reimbursement amount and how the amount was calculated is presented to the user (step 218).

FIG. 2B represents and out-patient claim. The claim is received and is processed through the CMS Out-Patient Code Editor (OCE) to review coding accuracy (step 220). Edits are applied to line items at the HCPCS level (step 222). The out-patient process examines each claim line and then benchmarks each HCPCS to a national or peer group median cost value (step 224). Costs of all comparison cases are then adjusted based on hospital's wage index (step 226). Using a pre-selected method, the initial target reimbursement amount is calculated by summing the line item medial benchmark costs from the claim and applying an additional margin factor (228). Any applicable override rules and/or inflation factors are then applied (step 230) to arrive at the reimbursement amount (232). All relevant information on reimbursement amount and how the amount was calculated is presented to the user (step 234).

More specifically, the process begins when a claim is submitted to the system. A Refined DRG (rDRG) is assigned to in-patient claims by comparing cases based on segmentation into the Yale Refined DRG (rDRG) methodology. Segmentation is based on the presence or absence of comorbitities, complications, and patient age. This results in every case being assigned a severity level of 0, 1, 2 or 3. Level 0 represents 'mild to no complicating condition.' Level 1 represents 'moderate complicating condition.' Level 2 represents 'severe complicating condition.' Level 3 represents 'catastrophic complicating condition.' Similar cases are compared. For example, a claim representing a severity level 2 case will only be compared with the level 2 cases in the comparison hospitals.

Full cost to the hospital or other provider (simply referred to as "hospital" hereinafter) in providing care for a case is calculated using the most recently available cost-to-charge ratios (CCRs) by department, as provided to Medicare by the hospital. The cost is determined for benchmarking purposes and incorporation in the reimbursement methodology. For comparison purposes, each hospital inpatient claim to be re-priced is compared to a benchmark group of similar clinical cases, in 'like' hospitals, over the most recently available 24 months. In determining 'like' hospitals, factors include, but are not limited to, bed size, teaching vs. non-teaching, and rural vs. urban. The recommended approach is to match on all 'like' attributes. Benchmarking is established for comparisons and incorporation into the reimbursement methodology. Benchmarking out-patient claims may be done at the HCPCS line level across all hospitals at the national level regardless of bed type.

The calculation of fair reimbursement for either an in-patient and out-patient claim incorporates the use of a client-selected methodology (see Table 1) in the next step. The client may select one of seven reimbursement methodology options. Finally, any overrides and/or inflation factor may be applied. Once the claim reimbursement is determined, information is returned to the client. In the exemplary screen shot of FIG. 3, the transparency is provided by showing the total submitted charges along with the comparison data and an explanation of the methodology used. The exemplary comparison data in FIG. 3 includes a statement of the hospital's cost of care, the Medicade Standard reimbursement amount, and the claim reimbursement provided by Data iSight System 100. The exemplary explanation of methodology includes the annotation on the hospital cost of care (estimated from the hospital's cost report and applied cost-to-charge rations) and the Data iSight reimbursement amount (as a percentage of the standard Medicare reimbursement). Thus, the results of Data iSight System 100 may include, but are not limited to, rDRG assignment, cost of care calculations, benchmarking of facilities, and the reimbursement methodology used. The claim is then closed.

TABLE 1

Available Methods

| | |
|---|---|
| F1 | Reimbursement at which X % of Hospitals are profitable |
| F2 | Reimbursement at which the average mark-up is X % |
| F3 | Reimbursement at X % of Cost |
| F4 | Reimbursement at X % of Medicare Reimbursement |
| F5 | Reimbursement at X % of Charges |
| F6 | Reimbursement at X Percentile of Billed Charges |
| F7 | Reimbursement at Average Billed Charges |

Available Overrides

| | |
|---|---|
| O1 | Don't Pay Less Than X % of Claim's Cost |
| O2 | Don't Pay Less Than X % of Claim's Charge |
| O3 | Don't Pay Less Than X % of Claim's Reimbursement |
| O4 | Don't Pay More Than X % of Claim's Cost |
| O5 | Don't Pay More Than X % of Claim's Charge |
| O6 | Don't Pay More Than X % of Claim's Reimbursement |
| O7 | Don't Pay More Than Billed Charges |

Figure 4:
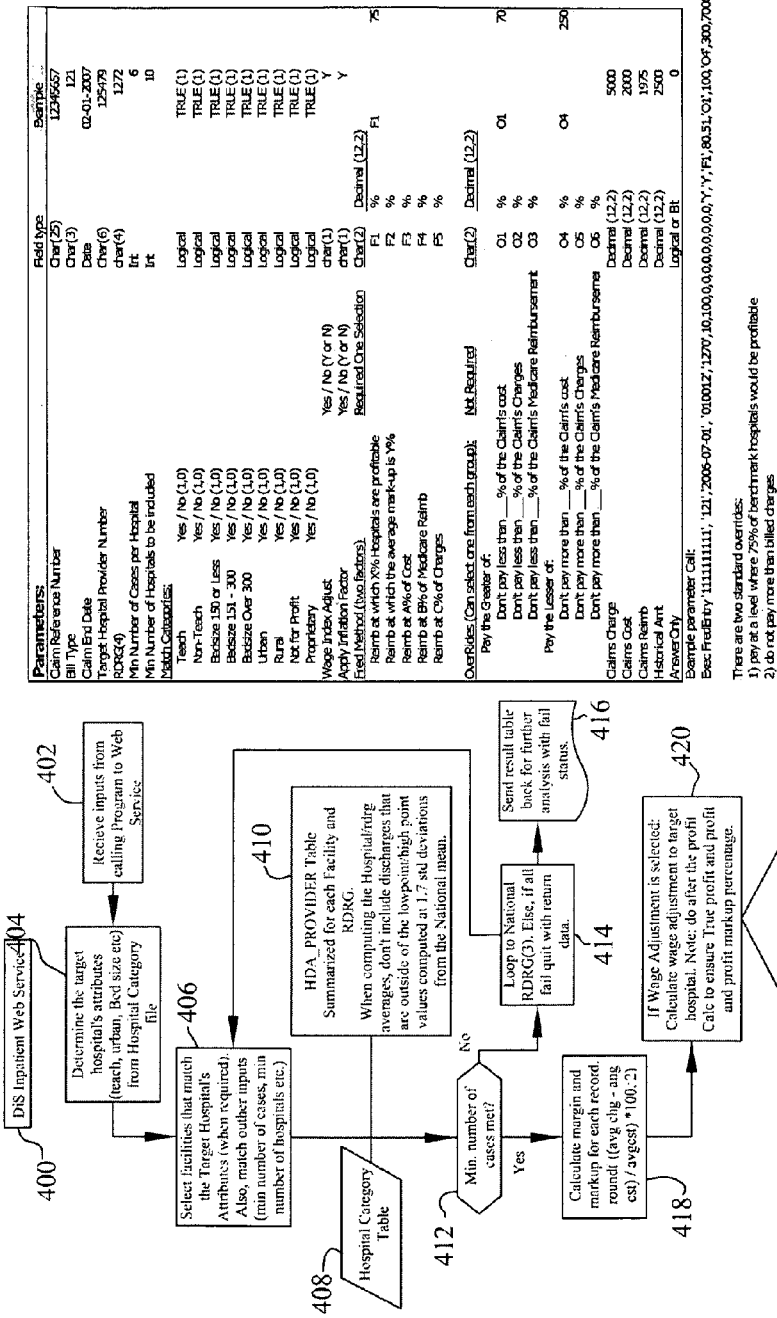
FIG. 4 is a flow chart diagram illustrating another exemplary method for determining the reimbursement amount.

A more specific embodiment of the invention is shown in FIG. 4. In this embodiment, a server based computer receives inputs from a calling program in step 402. These inputs may be defined by an XML coded message, or may have another data structure, with information relating to the claim, the hospital, and the reimbursement calculation method. With the received inputs, the server determines the subject hospital attributes from the inputs in step 404, and selects hospitals that match the subject hospital in step 406. The selection step 406 also includes matching certain characteristics of the hospital for comparison purposes, making sure a minimum matching criteria is present (for example, a minimum number of cases per hospital, a minimum number of hospitals). The comparison is made against the records in the Hospital Category Table 408. Further, the rDRG is obtained from the input and corresponding records from matching hospitals are assembled in step 410, wherein rDRG averages are calculated from matching hospital records of the same rDRG. Step 410 also filters out any outlier rDRG records having cost data more that 1.7 standard deviations from the National mean.

The server tests if a minimum number of cases have been selected in check step 412. If an insufficient number of rDRG records are present from the matched hospitals after filtering out the outlier records, then in step 414 the selection process is started anew in step 406, but with a national scope of hospitals rather than a more geographically focused scope of hospitals from the original inquiry. If in step 412 there are still an insufficient number of rDRG records then step 414 sends the result table back to the calling program with the indication of the fail status of the reimbursement calculation.

Assuming that a sufficient number of rDRG records are found in step 412, the markup and margin may be calculated for each rDRG record by the equation:

$$(((\text{Average Charge})-(\text{Average Cost}))/(\text{Average Cost}))*100$$

Once the markup and margin is calculated, step 420 may be used to perform a Wage Adjustment. The resulting sample set is used to create a table in step 422, and a table is returned with inputs and matching attributes in step 424. In step 426 the server checks which methodology (see Table 1) is to be used and starts the appropriate calculation in the methodology step 428.

Figure 5:
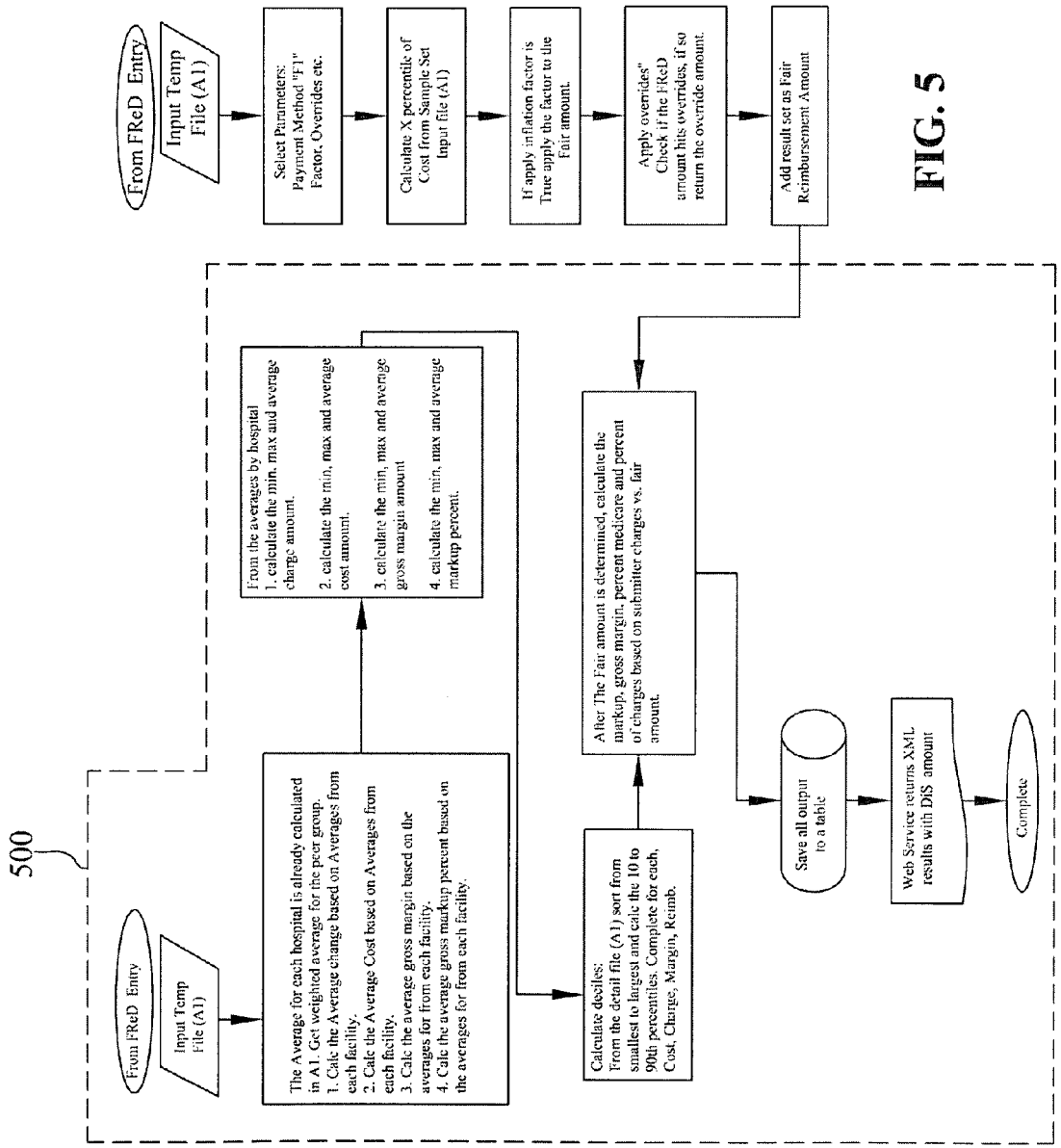
FIGS. 5-11 are flow chart diagrams illustrating methods for calculating the reimbursement amount.
Figure 6:
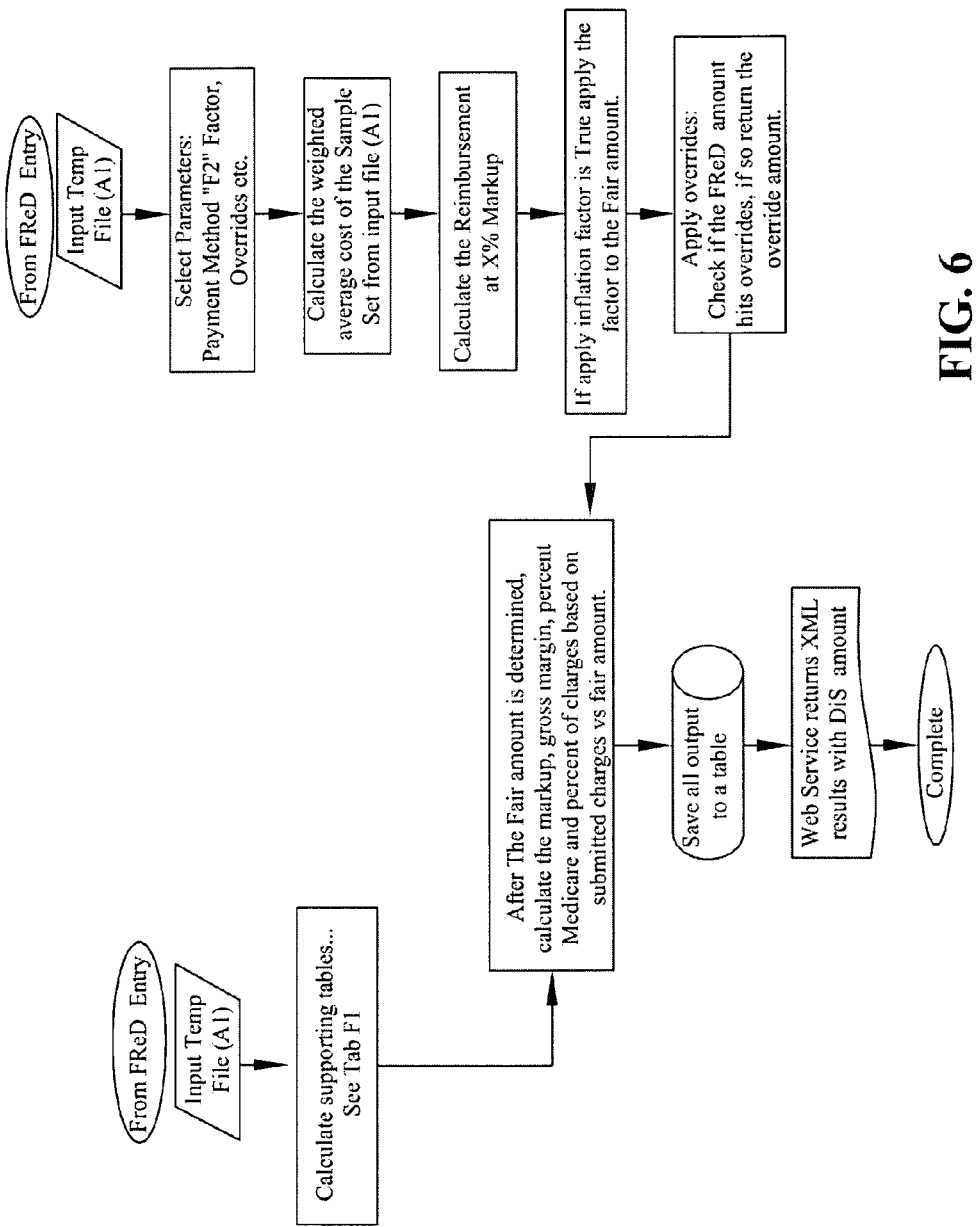
Figure 7:
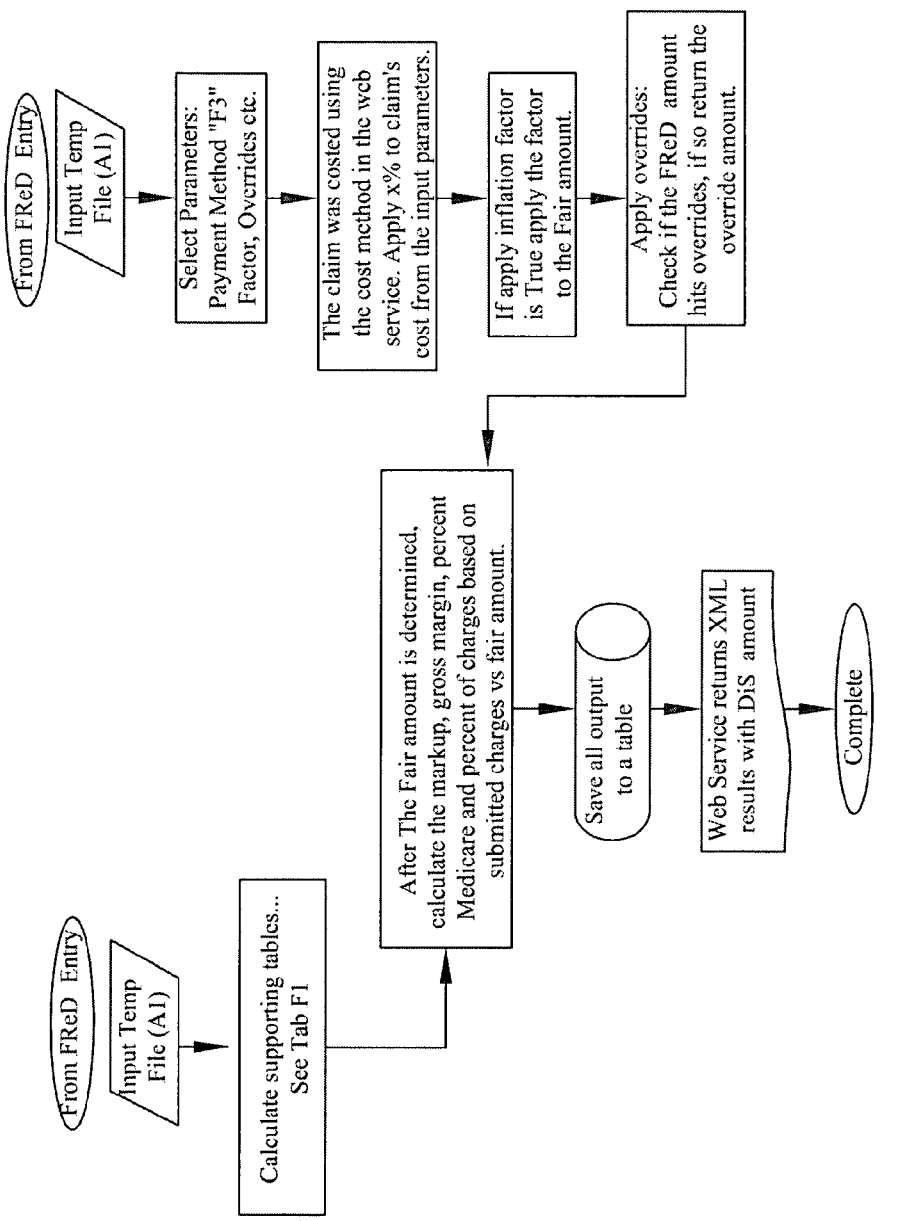
Figure 8:
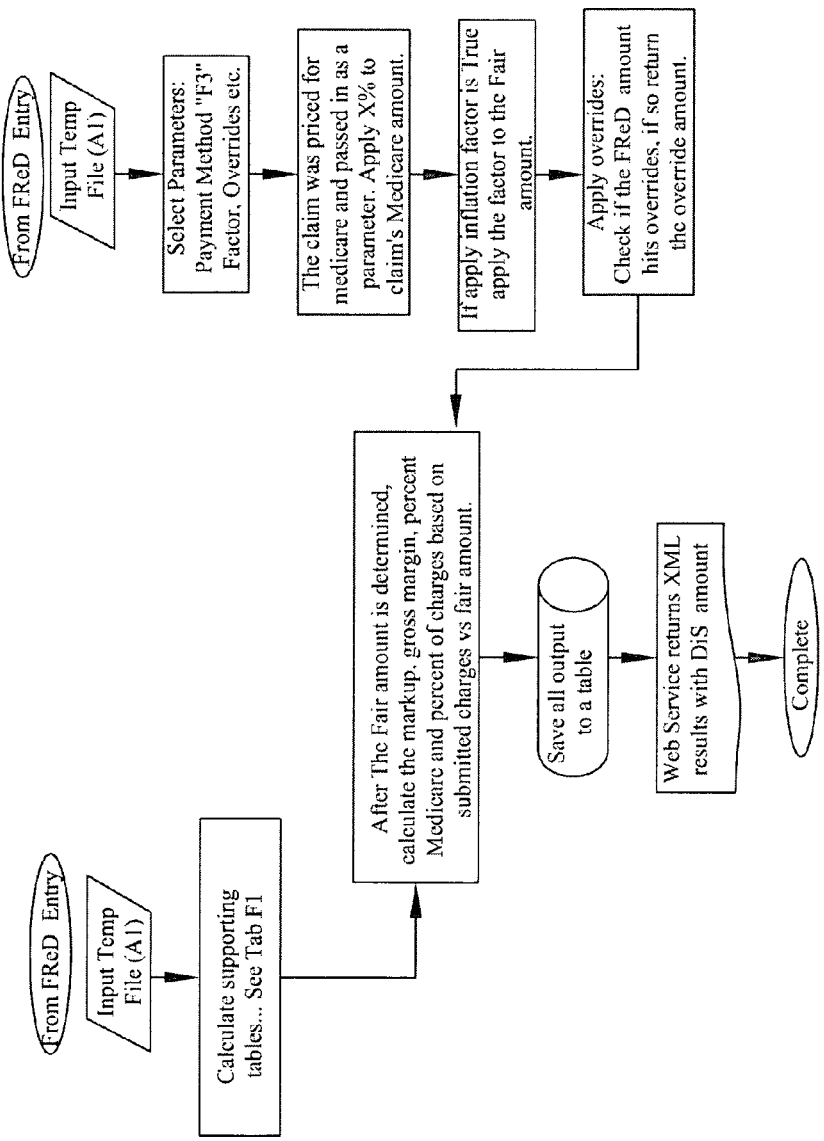
Figure 9:
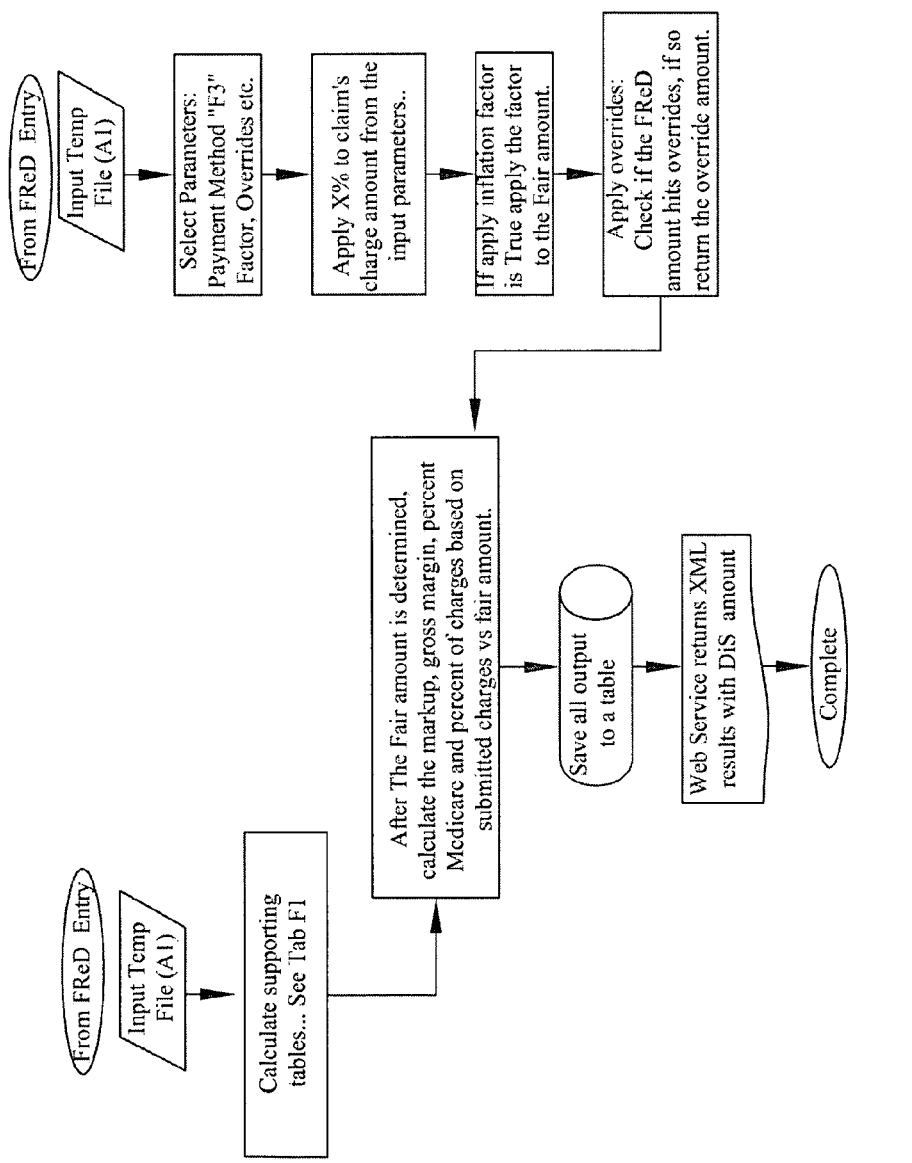
Figure 10:
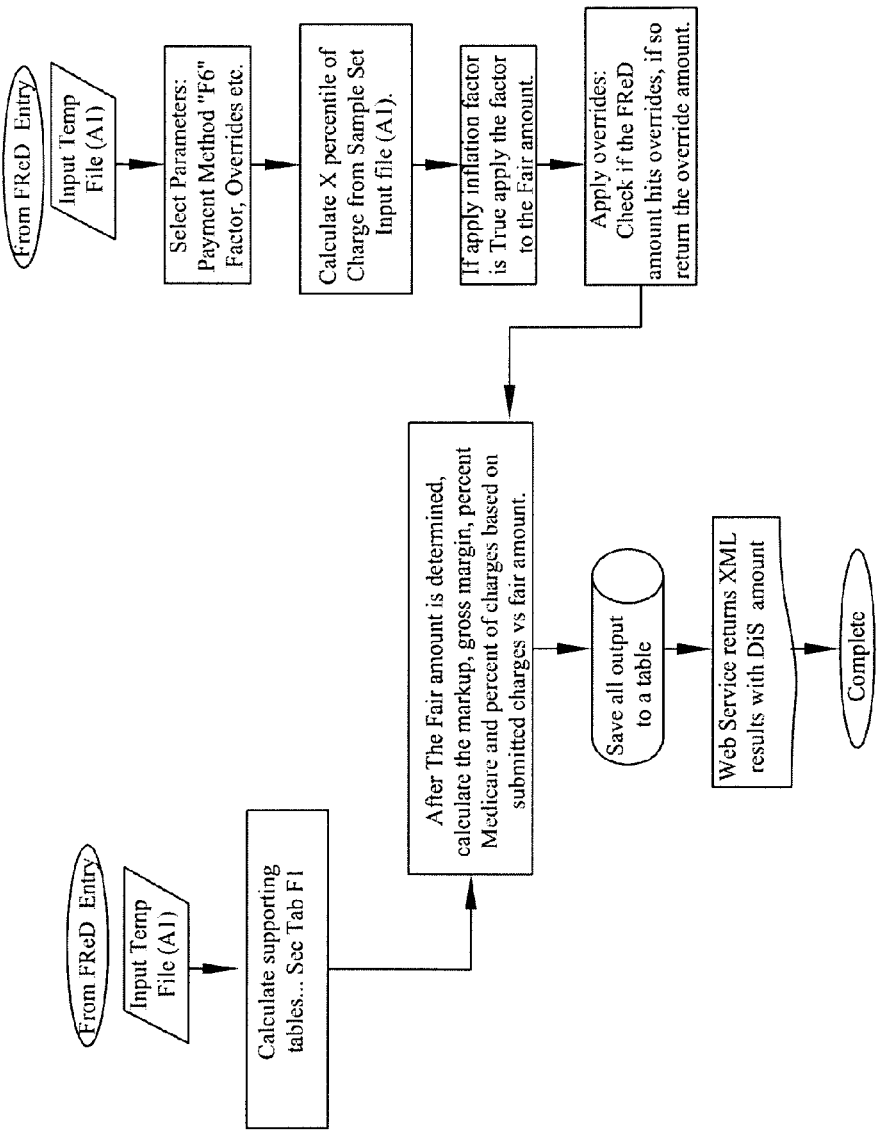
Figure 11:
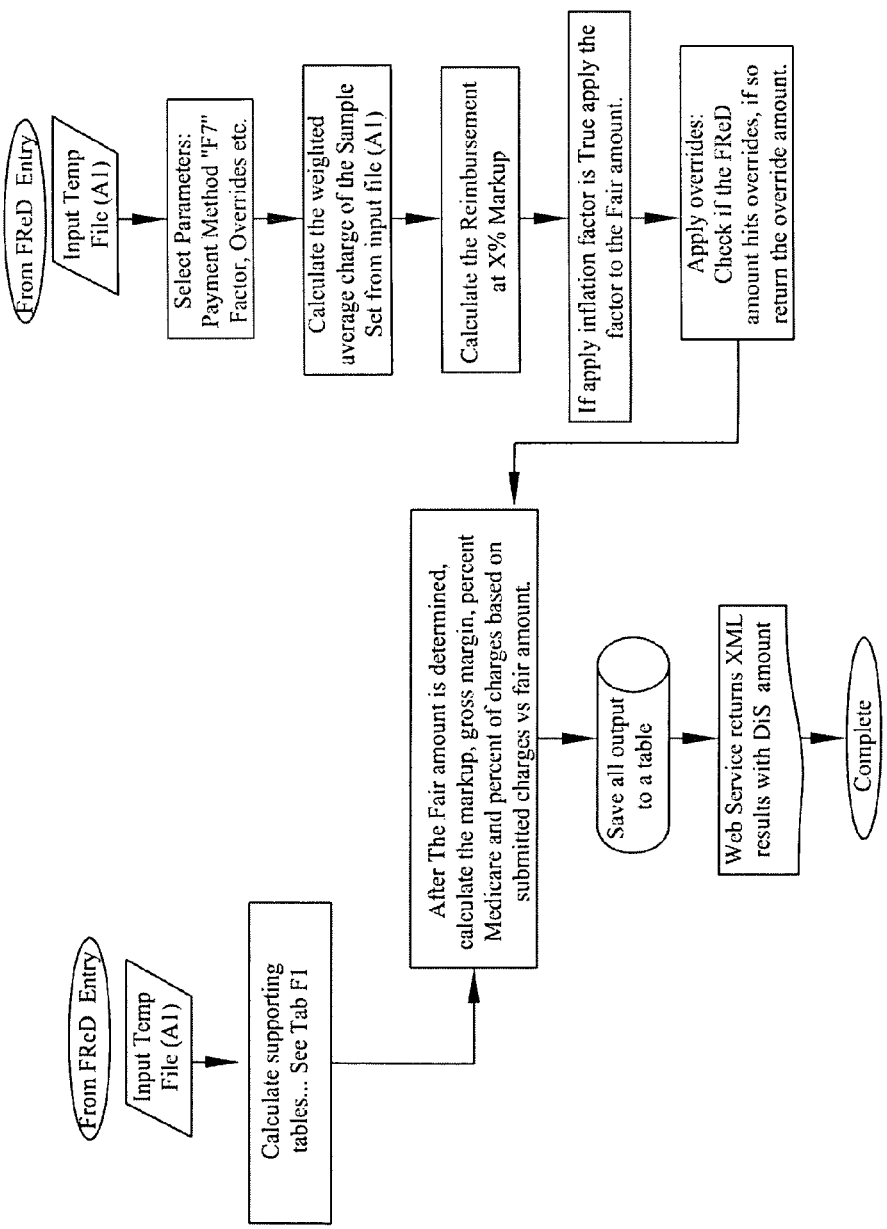

One of seven methodologies may be used in computing the reimbursement amount. The list of methodologies is shown above in Table 1, and are described in detail in FIGS. 5-11. Each methodology employs the calculation of supporting tables, and an exemplary method of preparing such tables is shown in section 500 of the flow chart of FIG. 5. The supporting tables generally include data from reference hospitals or health care providers which is sorted for minimum and maximum values, with the calculation of averages and percentile numbers.

Data iSight methodology F1 calculates the reimbursement amount at a level where X % of hospitals are profitable. Costs for all discharges in the benchmark group are compared (like hospitals, same rDRG). The level of reimbursement is determined that would make X % (for example, 90%) of the benchmark hospitals profitable using wage adjusted cost for each hospital in the benchmark group. Using this methodology, the reimbursement level is only slightly above cost. This method may be used to reward efficient hospitals.

Data iSight methodology 2, for inpatient claims, calculates the reimbursement amount at a level where the average mark-up of the benchmark group is X %. For illustrative purposes, 150% is used. Costs for all discharges in the benchmark group are compared. All discharges are arranged in deciles. A decile is one of ten segments of a distribution that has been divided into tenths. The average cost of all benchmark discharges is determined and multiplied by 150%. This methodology may be used to reward efficient hospitals and provide an average cost+50% profit (in this example). Data iSight Methodology 2, for outpatient claims, calculates the reimbursement amount at a level where the average mark-up of the benchmark group is X %. For illustrative purposes, 150% is used. Costs for each line level HCPCS in the benchmark group are compared and a median costs is calculated. The median cost is then multiplied by 150%. This methodology may used to reward efficient hospitals and provide an average cost+50% profit (in this example).

Data iSight methodology 3 calculates the reimbursement at X % (for example, 140%) above cost of a specific hospital. The cost for a specific claim at a specific hospital is determined and multiplied by 140%. This method ensures the same margin for all claims/hospitals. This method would not be used to provide more efficient hospitals with an advantage.

Data iSight methodology 4 calculates the reimbursement amount at X % (for example, 250%) of Standard Medicare reimbursement for this specific claim at a particular hospital. The Medicare reimbursement is determined for a specific hospital and specific claim, including outlier and Disproportionate Share Adjustment (DSH) calculations. DSH is a payment adjustment under Medicare's prospective payment system (PPS) for Medicaid utilization at hospitals that serve a relatively large volume of low-income patients, pregnant patients or other patients under the Medicaid program. The amount is multiplied by 250% in this example. This method may be used to comport with the current HDA product and Medicare percentage.

Data iSight methodology 5 calculates the reimbursement amount at X % (for example, 80%) of the billed charge. The reimbursement amount is calculated for the specific claim and hospital. This method may be used as a valuable tool for comparison purposes.

Data iSight methodology 6 calculates reimbursement at X percentile (for example, $75^{th}$ percentile) of a benchmark group's billed charges. Charges for all discharges are determined in the benchmark group. The charge is adjusted using a proprietary charge index, which may be obtained from analysis of known data, or from a third party index provider, or from a combination of these two. All discharges in the benchmark group are arranged in deciles. The selected percentile is determined and applied to the specific claim. This method may be used for clients with usual and customary charge language. For an outpatient claim, Data iSight methodology 6 calculates reimbursement at X percentile (for example, $75^{th}$ percentile) of a benchmark group's billed charges. Charges for all HCPCS codes are determined in the benchmark group. The charge is adjusted using a proprietary charge index, which may be obtained from analysis of known data, or from a third party index provider, or from a combination of these two. Each HCPCS code in the benchmark group is arranged in deciles. The selected percentile is determined and applied to the specific claim line. This method may be used for clients with usual and customary charge language.

For inpatient claims, using Data iSight methodology 7 the reimbursement amount is calculated using the average billed charge of the benchmark group. First, the charges of all discharges are determined in the benchmark group. The charge is adjusted based on proprietary charge index. The average charge of the benchmark group is determined The average charge is applied to the specific claim. This method may be used for clients with 'charge' policy language.

For outpatient claims, Data iSight methodology 7 the reimbursement amount is calculated using the average billed charge of each HCPCS code in the benchmark group. First, the charges of each HCPCS code is determined in the benchmark group. The charge is adjusted based on proprietary charge index. The average charge of each HCPCS code for the benchmark group is determined. The average charge of each line is added and applied to the specific claim. This method may be used for clients with 'charge' policy language.

In another embodiment, one of seven Overrides may be used. The list of overrides is shown in Table 1. Each override may be independently implemented if desired. Each override involves comparing the calculated fair value with an element of a claim, and if the comparison test is satisfied then a specified value is substituted for the calculated fair value. For example, with override O3 (Don't Pay Less Than X % of Claim's Reimbursement), the calculated fair value is compared to the standard Medicare/Medicade Reimbursement amount for this type of claim multiplied by 130%. If the result of the comparison is that the calculated fair value is less, then the X % of the standard Reimbursement amount would be used in place of the previously calculated fair value.

An Inflation Factor may also be used in the calculations of the fair reimbursement amount. Initially, the inflation factor may be set at a default value, such as 5%. Alternatively, the inflation factor may be set to a predetermined index, such as the Employment Cost Index (ECI) wage and benefit data for hospital workers, or other suitable index. The inflation factor may be added to costs to account for increases in wages, supplies, etc.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:

1. A server for calculating a reimbursement amount for a health care claim, comprising:
    a computer processor and associated memory;
    an input module encoded on a computer-readable medium assessable by said computer processor for enabling said computer processor to receive medical claim data from a hospital;
    a database stored on said memory containing hospital cost benchmarking data;
    a benchmarking module encoded on the computer readable medium configured to calculate the hospital cost benchmarking data by grouping inpatient medical claims into one or more benchmark groups based on a refined diagnosis related group assignment and a severity classification assignment,
        wherein the one or more benchmark groups classify the inpatient medical claims into classifications of severity based on co-morbidities and complications and their impact on resource use; and
        wherein the inpatient medical claims are further grouped into similar hospital groups wherein similar hospitals are hospitals having similar attribute data including having bed capacities that match a user selected range for the number of beds in the hospital, having a matching classification as a teaching or non-teaching hospital, and having a matched urban or rural location; and
    said computer processor capable of calculating the reimbursement amount for the received medical claim, wherein a methodology module is encoded on the computer-readable medium and enables said computer processor to apply a pre-selected calculation methodology in calculating the reimbursement amount based upon the received medical claim data and hospital cost benchmarking data; the pre-selected calculation methodology including:
        1) comparing an inpatient medical claim to the one or more benchmark groups having the same diagnosis related group assignment and severity classification assignment and
        2) grouping outpatient medical claims into ambulatory patient classification assignments; and
        3) calculating the reimbursement amount for the received medical claim based on the comparison, and
    an output module is encoded on the computer-readable medium and enables said processor to provide the reimbursement amount and hospital cost benchmarking data to the hospital.

2. The server of claim 1 further comprising a database for storing the received medical claim data and hospital cost benchmarking data.

3. The server of claim 1, wherein the processor further includes a rating module encoded on the computer-readable medium and enabling said processor to generate diagnosis group data rated for severity based upon the medical claim data.

4. The server of claim 1, wherein the processor further includes a median cost value module encoded on the computer-readable medium and enabling said processor to calculate a median cost value based on at least one of a national or peer group cost value.

5. The server of claim 4 wherein the median cost value module includes an adjustment module encoded on the computer-readable medium and enabling said processor to augment the median cost value by a factor related to a hospital wage index.

6. The server of claim 1, wherein the processor further includes a cost calculator module encoded on the computer-readable medium and enabling said processor to generate cost of care data based upon the medical claim data, hospital attribute data and Medicare data and the cost of care data is used by the methodology module in calculating the reimbursement amount.

7. The server of claim 1, wherein the processor further includes an adjustment module encoded on the computer-readable medium for enabling said processor to calculate adjustments to the reimbursement amount based upon overrides and/or inflation factors.

8. The server of claim 1 wherein said output module further provides an explanation of the methodology used to calculate the reimbursement amount.

9. The server of claim 1, wherein the pre-selected calculation methodology calculates the reimbursement amount at a level intended to make a defined percentage of hospitals profitable on the claim.

10. The server of claim 1, wherein the pre-selected calculation methodology calculates the reimbursement amount such that an average markup over cost of a benchmarking group is a defined percentage.

11. The server of claim 1, wherein the pre-selected calculation methodology calculates the reimbursement amount as a defined percentage above the cost at a chosen hospital.

12. The server of claim 1, wherein the pre-selected calculation methodology calculates the reimbursement amount as a defined percentage of Standard Medicare reimbursement for the claim at a particular hospital.

13. The server of claim 1, wherein the pre-selected calculation methodology calculates the reimbursement amount as a defined percentage of the billed charge.

14. The server of claim 1, wherein the pre-selected calculation methodology calculates the reimbursement amount in relation to a defined percentile of a benchmark group's billed charges.

15. The server of claim 1, wherein the pre-selected calculation methodology calculates the reimbursement amount using the average billed charge of the benchmark group.

16. A method for calculating a reimbursement amount, comprising the steps of:
obtaining a hospital cost benchmarking database including a plurality of hospital cost benchmarking data records readable by a computer;
wherein the hospital cost benchmarking data is calculated by grouping inpatient medical claims into one or more benchmark groups based on a refined diagnosis related group assignment and a severity classification assignment,
wherein the one or more benchmark groups classify the inpatient medical claims into classifications of severity based on co-morbidities and complications and their impact on resource use; and
wherein the inpatient medical claims are further grouped into similar hospital groups wherein similar hospitals are hospitals having similar attribute data including having bed capacities that match a user selected range for the number of beds in the hospital, having a matching classification as a teaching or non-teaching hospital, and having a matched urban or rural location; and receiving medical claim data from a hospital and entering the medical claim data in the computer;
calculating the reimbursement amount using the computer that includes computer-readable media with a computer program enabling execution of a pre-selected methodology in calculating the reimbursement amount based upon the received medical claim data and hospital cost benchmarking data; the pre-selected calculation methodology including:
1) comparing an inpatient medical claim to the one or more benchmark groups having the same diagnosis related group assignment and severity classification assignment and
2) grouping outpatient medical claims into ambulatory patient classification assignments; and
3) calculating on the computer the reimbursement amount for the received medical claim based on the comparison, and
providing the reimbursement amount and hospital cost benchmarking data to the hospital.

17. The method of claim 16 further comprising the step of storing the reimbursement amount and reimbursement amount benchmarking data in a database.

18. The method of claim 16, further comprising the step of:
generating diagnosis group data rated for severity based upon the medical claim data.

19. The method of claim 16, further comprising the step of:
calculating on the computer median cost value data based on at least one of a national or peer group cost value.

20. The method of claim 19, further comprising the step of:
adjusting the median cost value data by a factoring a related hospital wage index.

21. The method of claim 16, further comprising the step of:
calculating on the computer cost of care data based upon the medical claim data, hospital attribute data and Medicare data wherein the cost of care data is used in calculating the reimbursement amount.

22. The method of claim 16 further comprising the step of:
applying adjustments to the reimbursement amount on the computer based on overrides and/or inflation factors.

23. The method of claim 16 further comprising the step of:
determining a baseline amount using the computer at which a predetermined percentage of Hospitals are profitable; and
calculating on the computer the reimbursement amount based upon the baseline amount.

24. The method of claim 16 further comprising the step of:
calculating on the computer an average mark-up amount at a predetermined percentage; and
calculating on the computer the reimbursement amount using the average mark-up amount.

25. The method of claim 16 further comprising the step of:
calculating on the computer a baseline amount using a predetermined percentage of cost; and
calculating on the computer the reimbursement amount based upon the baseline amount.

26. The method of claim 16 further comprising the step of:
calculating on the computer a baseline amount using a predetermined percentage of Medicare Reimbursement; and
calculating on the computer the reimbursement amount based upon the baseline amount.

27. The method of claim 16 further comprising the step of:
calculating on the computer a baseline amount as a predetermined percentage of Charges; and
calculating on the computer the reimbursement amount based upon the baseline amount.

28. The method of claim 16 further comprising the step of:
calculating on the computer a baseline amount at a predetermined percentile of Billed Charges;
calculating on the computer the reimbursement amount based upon the baseline amount.

29. The method of claim 16 further comprising the step of:
calculating on the computer a baseline amount equal to average of billed charges; and
calculating on the computer the reimbursement amount based upon the baseline amount.

30. The method of claim 16 wherein the step of providing includes providing an explanation of the methodology used to calculate the reimbursement amount.

* * * * *

UNITED STATES PATENT AND TRADEMARK OFFICE
CERTIFICATE OF CORRECTION

| | | |
|---|---|---|
| PATENT NO. | : 8,103,522 B1 | Page 1 of 1 |
| APPLICATION NO. | : 12/163813 | |
| DATED | : January 24, 2012 | |
| INVENTOR(S) | : Thomas E. Galas et al. | |

It is certified that error appears in the above-identified patent and that said Letters Patent is hereby corrected as shown below:

In Claim 17, at column 14, line 29, please add a --,-- after the number "16".

In Claim 17, at column 14, lines 30-31, please delete the second occurrence of the words "reimbursement amount" and replace with --hospital cost--.

In Claim 17, at column 14, lines 30-31 should read as follows:

"The method of claim 16, further comprising the step of storing the reimbursement amount and hospital cost benchmarking data in a database."

Signed and Sealed this
Twenty-fourth Day of July, 2012

David J. Kappos
*Director of the United States Patent and Trademark Office*